(12) United States Patent
Tsukahara et al.

(10) Patent No.: US 7,244,224 B2
(45) Date of Patent: Jul. 17, 2007

(54) PUMP DRIVING UNIT FOR DRIVING A PUMP USED FOR SUPPORTING OR SUBSTITUTION OF CARDIAC FUNCTION

(75) Inventors: Kinji Tsukahara, Seki (JP); Hideki Wakui, Anjo (JP); Katsuya Tsuchimoto, Anjo (JP); Akira Suzuki, Nishio (JP)

(73) Assignee: Senko Medical Instrument Mfg. Co., Ltd., Tokyo (JP)

( * ) Notice: Subject to any disclaimer, the term of this patent is extended or adjusted under 35 U.S.C. 154(b) by 563 days.

(21) Appl. No.: 10/609,612

(22) Filed: Jul. 1, 2003

(65) Prior Publication Data
US 2004/0092789 A1 May 13, 2004

Related U.S. Application Data

(63) Continuation of application No. 09/843,858, filed on Apr. 30, 2001, now abandoned.

(30) Foreign Application Priority Data

Apr. 28, 2000 (JP) .............................. 2000-129596
Mar. 15, 2001 (JP) .............................. 2001-074968

(51) Int. Cl.
*A61M 1/12* (2006.01)
*A61M 1/10* (2006.01)

(52) U.S. Cl. ..................... 600/16; 601/150; 623/3.21
(58) Field of Classification Search .............. 600/16, 600/17; 601/148, 149, 150; 623/3.1, 3.16, 623/3.18, 3.19, 3.2, 3.21, 3.24–3.26
See application file for complete search history.

(56) References Cited

U.S. PATENT DOCUMENTS

| 4,974,774 A | * | 12/1990 | Nakagawa et al. ........... 600/18 |
| 5,064,353 A | * | 11/1991 | Tsukahara ................... 417/383 |
| 5,269,811 A | | 12/1993 | Hayes et al. |
| 5,282,849 A | | 2/1994 | Kolff et al. |
| 5,513,956 A | | 5/1996 | Lewis et al. |
| 5,766,207 A | | 6/1998 | Potter et al. |

FOREIGN PATENT DOCUMENTS

JP          11-188091       7/1999

* cited by examiner

*Primary Examiner*—Carl Layno
*Assistant Examiner*—Frances P. Oropeza
(74) *Attorney, Agent, or Firm*—Oblon, Spivak, McClelland, Maier & Neustadt, P.C.

(57) ABSTRACT

In a small sized pump driving unit, a fluid pump is used for driving the pump for supporting of substituting of cardiac function. The fluid pump can generate pressure fluctuations that can generate pulsation of the pump for supporting or substituting of cardiac function and produces sufficient performance to drive the pump unit.

11 Claims, 2 Drawing Sheets

PUMP DRIVING UNIT FOR DRIVING A PUMP USED FOR SUPPORTING OR SUBSTITUTION OF CARDIAC FUNCTION

This application is a continuation of application Ser. No. 09/843,858 filed on Apr. 30, 2001, now abandoned. The entire disclosure of Japanese Patent Applications No. 2000-129596 filed on Apr. 28, 2000 and No. 2001-074968 filed on Mar. 15, 2001, including the specification, drawings and abstract, is incorporated herein by reference in its entirety.

BACKGROUND OF THE INVENTION

1. Field of the Invention

The present invention generally relates to a pump driving unit for driving a pump used for supporting or substituting of cardiac function, such as a blood pump which is applied to an artificial heart or an intra-aortic balloon pump which supports cardiac function. More particularly, this invention provides for miniaturization of the pump driving unit.

2. Description of the Background

A known type of a pump driving unit for driving a pump used for supporting or substitution of cardiac function, such as a blood pump or IABP (Intra-Aortic Balloon Pump) is disclosed in Japanese Patent Laid-Open Publication No.11-188091. This publication discloses an air pressure driven type pump driving unit, which drives a pump used for an artificial heart.

A conventional air pressure driven type pump driving unit such as the above cited publication, generally has a compressor, a high pressure accumulation chamber and a low pressure accumulation chamber, and is placed outside of a human body. The high pressure accumulation chamber is connected to an output port of the compressor and the low pressure accumulation chamber is connected to an intake port of the compressor, respectively. These two accumulation chambers are connected to a connection port of the artificial heart through a selector valve. In response to operation of the selector valve, these accumulation chambers are selectably communicated with the connection port, and pressure fluctuation thereby occurs. The pressure fluctuation which is generated between these pressure accumulation chambers drives a pump used for supporting or substitution of cardiac function.

The conventional air pressure driven type pump driving unit must have a compressor, and high and low pressure accumulation chambers, and so is bulky. To reduce the size of the driving unit, U.S. Pat. No. 5,766,207 suggests placing the compressor in the low pressure accumulation chamber. However, the unit still requires a compressor and a low pressure accumulation chamber, which limits the size reduction of the pump driving unit. Since the pump driving unit must always accompany the user, this limits the user's range of activity.

SUMMARY OF THE INVENTION

In view of above mentioned disadvantage of the conventional driving unit, it is an object of the present invention to produce a pump driving unit that has minimized unit size.

To achieve the above and other objects, a pump driving unit for driving a pump used for supporting or substitution of a cardiac function comprises a fluid pump which is a driving source of the pump used for supporting or substitution of a cardiac function.

Further, the pump driving unit for driving a pump used for supporting or substituting of cardiac function comprises an isolator forming therein a first space, and a second space divided from the first space by a flexible member and connected to the pump, a fluid pump connected to the first space and operated so as to supply a fluid media therein to the first space or to suck a fluid media into the first space, and a control unit for controlling an operation of the fluid pump.

The fluid pump generates sufficient pressure fluctuations to generate pulsative operation of the pump used for supporting or substitution of cardiac function such as the blood pump or the balloon pump, and need not use an accumulation chamber to adjust the pressure. Therefore, the pump driving unit can have a small size. Further, the fluid pump is smaller than a compressor so that the size of the pump driving unit can be minimized.

BRIEF DESCRIPTION OF THE DRAWINGS

Additional features and characteristics of the present invention will become more apparent from the following detailed description considered with reference to the accompanying drawing figures in which like elements are designed by like reference numerals and wherein.

DETAILED DESCRIPTION OF THE INVENTION

This invention will be described in according to preferred embodiments which are shown in attached drawings.

First Embodiment

Figure 1:
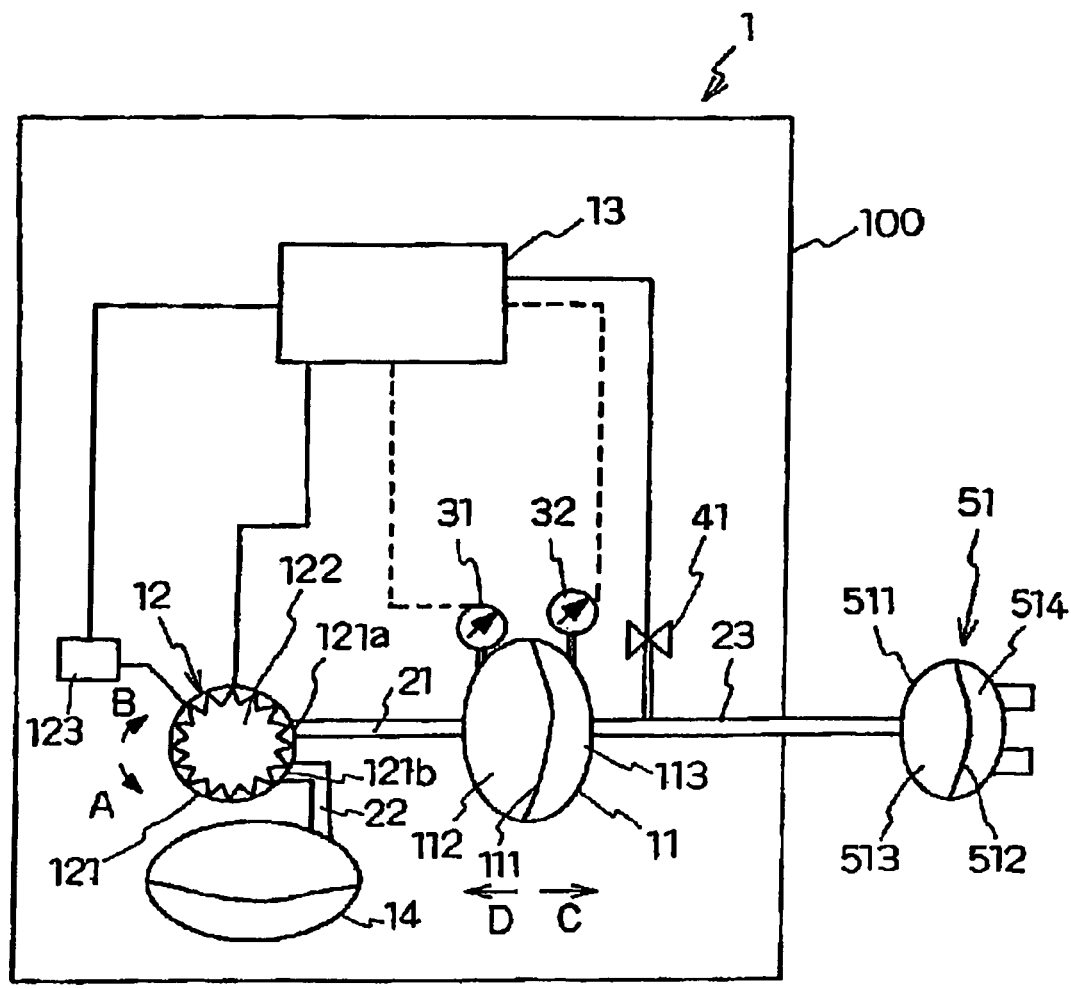
FIG. 1 illustrates a structure of the first embodiment of a pump driving unit according to the invention.

FIG. 1 shows a schematic structure of the first embodiment of the invention. A pump driving unit 1 has an isolator 11, a fluid pump 12, a control unit 13 and a reservoir tank 14. The aforementioned elements are retained in a housing 100 of a pump driving unit 1.

The interior of the isolator 11 is divided into a first space 112 and a second space 113 by a flexible member such as a diaphragm 111. In this embodiment, the diaphragm 111 is made from fluorine rubber material.

The fluid pump 12 pulsatively drives a blood pump 51. In other words, the fluid pump 12 is used as a driving source of the blood pump 51. A turbine type fluid pump 12 is used in this embodiment. An impeller turbine 122 is disposed in a pump housing 121. The fluid pump 12 rotates in both clockwise and counterclockwise directions. The pump housing has a first port 121a and a second port 121b. The first port 121a communicates with the first space 112 of the isolator 11 through a fluid path 21. The second port 121b communicates with the reservoir tank 14 through a fluid path 22. The impeller turbine 122 is driven by a motor 123. The motor 123 drives the impeller turbine 122 bidirectionally, that is, in either a clockwise direction (shown by arrow B in FIG. 1) or a counterclockwise direction (shown by arrow A in FIG. 1). The rotational speed of the motor 123 is variably controlled through the control unit 13. A brushless motor or a stepping motor can be used as the motor 123 in this embodiment.

A first pressure sensor 31 is arranged at the first space 112 and a second pressure sensor 32 is arranged at the second space 113 to detect actual pressure levels in these spaces. The detected actual pressure levels in the isolator are transmitted to the control unit 13.

The second space 113 communicates with the blood pump 51 through a fluid path 23. An intake and exhaust control valve 41 is mounted in the path 23 to control a pressure level in the path 23. A two way (open-close) valve is used in this embodiment, and the valve 41 is controlled by the control unit to retain the pressure level in the path 23 within a predetermined range.

The control unit 13 controls the operation of the fluid pump 12 through the motor 123 and the operation of the intake and exhaust control valve 41. In order to coordinate appropriate user conditions, the control unit 13 controls motor 123 and the intake and exhaust control valve 41 by using signals from first and second space pressure sensor 31 and 32. The motor 123 is controlled in its direction and speed, and the intake and exhaust control valve 41 is controlled in its open-close ratio.

The blood pump 51 has a housing 511 and a diaphragm 512. The inner space of the blood pump 51 is divided into a fluid chamber 513 and a blood chamber 514 by a diaphragm 512. The second space 113 of the isolator 11 is communicated with the fluid chamber 513 of the blood pump 51.

A liquid such as silicon oil is liquid tightly held in the first space 112, the path 21, the fluid pump 12, the path 22 and the reservoir tank 14. A gas such as air is gas tightly held in the second space 113, the path 23 and the fluid chamber 513 of the blood pump 51. Therefore, an upstream side (first side fluid) of the diaphragm 111 is contacted by silicon oil as a fluid media and a downstream (second side fluid) of the diaphragm 111 is contacted by air.

Operation of the first embodiment is described hereinafter. When the fluid pump 12 is driven in a counterclockwise (positive) direction (arrow A direction in FIG. 1), silicon oil in the fluid pump 12 is sent to reservoir tank 14 through the path 22 and silicon oil in the first space 112 is sucked by the fluid pump 12 through the path 21 and the first port 121a. In response to this operation, the pressure level in the first space 112 is decreased and the diaphragm 111 moves in the left direction (shown by arrow D) in FIG. 1. Consequently, the volume of the first space 112 is decreased and the volume of the second space 113 is expanded. According to the expansion of the volume of the second space 113, the pressure level in second space 113 will be reduced. This decompression is transmitted to the fluid chamber 513 of the blood pump 51 through the path 23 so that the volume of the fluid chamber 513 is decreased and the shape of the diaphragm 512 is transformed from the illustrated concave shape to a convex shape. As a result of this transformation of the shape of the diaphragm 512, the blood chamber 514 is pulsatively driven and blood is taken in.

When the fluid pump 12 is driven in a clockwise direction (negative direction) which means arrow B in FIG. 1, silicon oil in the reservoir tank 14 is sent to the fluid pump 12 through the path 22 and the second port 121b, and silicon oil in the fluid pump 12 is sent to the first space 112 through the first port 112a and the path 21. In response to this operation, the pressure level in the first space 112 is increased and the diaphragm 111 moves in the right direction (shown in arrow C) in FIG. 1. Consequently, the volume of the first space 112 is expanded and the volume of the second space 113 is decreased. According to the decreasing volume of the second space 113, the gas in the second space 113 will be compressed. This compression is transmitted to the fluid chamber 513 of the blood pump 51 through the path 23 so that the volume of the fluid chamber 513 is increased and the diaphragm 512 is transformed from a convex shape to a concave shape. In terms of this transformation of the diaphragm 512, the blood chamber 514 is pulsatively driven and blood is output from the fluid pump 51.

Due to this counterclockwise and clockwise rotation of the fluid pump, the blood pump 51 is pulsatively driven. The rate of fluid pump operation (cycle of between counterclockwise and clockwise operation) determines the pulse of the blood pump 51.

The transformation of the diaphragm 512, which includes the pulse operation of the blood pump 51, depends on the pressure level of the second space 113 and the fluid chamber 513. In this embodiment, the pressure levels in the second space 113 and the fluid chamber 513 is set to be within the range from −26.6 Kpa to +39.9 Kpa (equal to −200 mmHg to +300 mmHg). Pressure adjustment within the above described range and the rising or falling of the pressure level are controlled by the rotation speed of the fluid pump 12. The rotational speed of the fluid pump 12 is adjusted by controlling the output and/or intake amount of silicon oil. However, in the conventional pump driving unit, this pressure adjustment is performed by using a high pressure accumulation chamber and a low pressure accumulation chamber. In the present invention, the blood pressure in the blood pump 51 is appropriately adjust by controlling the rotational speed of the fluid pump 12, which eliminates the need for high and low pressure accumulation chambers.

Second Embodiment

Figure 2:
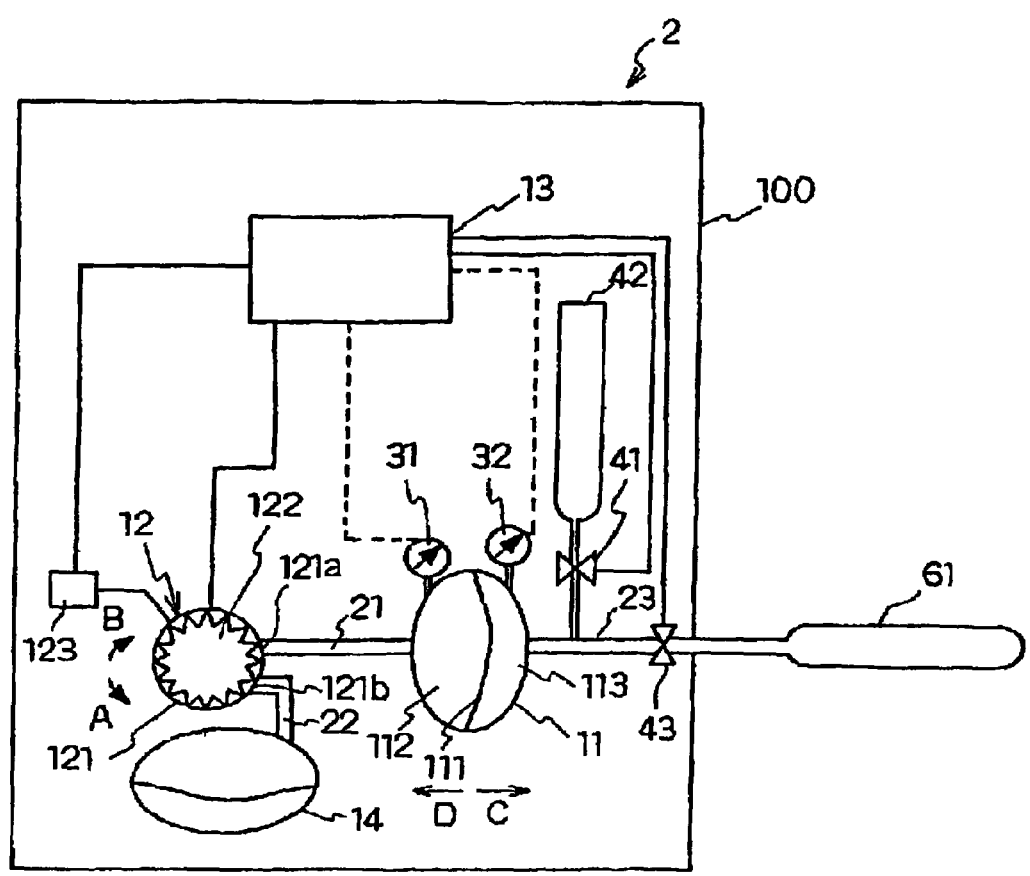
FIG. 2 illustrates a structure of the second embodiment of a pump driving unit according to the invention.

FIG. 2 shows a schematic structure of the second embodiment of the invention. In this second embodiment, a balloon pump driving unit 2 drives the balloon pump 61 instead of the blood pump 51. The same features as in the first embodiment are given the same numbers.

The balloon pump 61 is connected to the isolator 11 through the fluid path 23. The balloon pump 61 is installed in a patient's main artery (e.g., downstream main artery) and repeatedly shrinks and expands in response to the movement of the heart. The balloon pump 61 minimizes the burden of the heart and supports cardiac function.

A gas such as helium gas fills the second space 113, the path 23 and the balloon pump 61. Since helium gas is an inert gas, the gas is safe. Also, since it has low inertia, it enables high responsiveness for the balloon pump drive unit 2.

A helium gas storage cylinder 42 (means for helium gas supply to the balloon pump) is installed in the path 23 via an intake and exhaust control valve 41. When the amount of helium gas in the path 23 and/or the balloon pump 61 decreases, the helium gas storage cylinder 42 supplies additional helium gas.

As shown in FIG. 2, a pressure maintaining valve 43 is installed on the path 23 and is placed downstream of the intake and exhaust control valve 41. The pressure maintaining valve 43 controls the pressure in the balloon pump 61 by, and is controlled in its opening and closing by the control unit 13.

When the fluid pump 12 is driven in the counterclockwise direction (positive direction), which means arrow A in FIG. 2, silicon oil in the fluid pump 12 is sent to the reservoir tank 14 through the second port 121b and the path 22, and silicon oil in the first space 112 is sucked by the fluid pump 12 through the path 21 and the first port 121a. In response to this operation, the pressure level in the first space 112 is reduced and the diaphragm 111 moves in the left direction (shown by arrow D) in FIG. 2. Consequently, the volume of the first space 112 is decreased and the volume of the second space 113 is expanded. According to the expansion of the volume of the second space 113, the gas in the second space 113 will be decompressed. This decompression is transmitted to the balloon pump 61 through the path 23, and the volume of the balloon pump 61 is decreased and the balloon pump 61 shrinks.

When the fluid pump 12 is driven in the clockwise direction (negative direction), which means arrow B in FIG. 2, silicon oil in the reservoir tank 14 is sent to the fluid pump 12 through the path 22 and the second port 121b, and silicon oil in the fluid pump 12 is sent to the first space 112 through the first port 121a and the path 21. In response to this operation, the pressure level in the first space 112 is increased and the diaphragm 111 moves in the right direction (shown in arrow C) in FIG. 2. Consequently, the volume of the first space 112 is expanded and the volume of the second space 113 is decreased. According to the decreasing of the volume of the second space 113, the gas in the second space 113 will be compressed. This compression is transmitted to the balloon pump 61 through the path 23 and the volume of the balloon pump 61 is increased and the balloon pump 61 expands.

According to the counterclockwise and clockwise rotation of the fluid pump operation, the balloon pump 61 repeatedly expands and shrinks so that the balloon pump 61 supports blood flow and minimizes the burden of the heart and supports cardiac function.

In this embodiment, the pressure level in the balloon pump 61 is set within the range from −13.3 Kpa to +26.6 Kpa (equal to −100 mmHg to +200 mmHg). The pressure adjustment within the above described range and the rising or falling of the pressure level are controlled by rotation speed of the fluid pump 12. The rotational speed of the fluid pump 12 is adjusted by controlling the output and/or intake amount of silicon oil. In the conventional driving unit, this pressure adjustment is performed by using a high pressure accumulation chamber and a low pressure accumulation chamber. In the present invention, the blood pressure in the blood pump 51 is appropriately adjusted by controlling the rotational speed of the fluid pump 12, and so the high and low pressure accumulation chambers are unnecessary.

In this second embodiment, the pressure maintaining valve 43, which is controlled by the control unit 13, controls rapid pressure increasing and rapid pressure decreasing in the balloon pump fit.

The rapid pressure increasing is accomplished in accordance with following operation. When the balloon pump 61 is at a low pressure condition, the pressure maintaining valve 43 is closed by the control unit 13. The balloon pump 61 and the second space 113 of the isolator 11 are thus cut off from each other. Under this condition, the motor 123 drives the impeller turbine 122 in a clockwise direction (negative direction and shown an arrow B in FIG. 2) and silicon oil in the fluid pump 12 is supplied to the first space 112 of the isolator 11 so that the gas pressure level in the second space 113 is increased. The pressure level in the balloon pump 61 remains low because the pressure maintaining valve 43 is closed. When the pressure level in the second space 113 reaches a sufficiently high pressure level, the pressure maintaining valve 43 is opened by the control unit 13. In response to this operation, the accumulated pressure in the second space 113 is introduced into the balloon pump 61 in a burst and the pressure level in the balloon pump 61 rapidly changes from low pressure to high pressure.

A rapid pressure decrease is accomplished in accordance with following operation. When the balloon pump 61 is in a high pressure condition, the pressure maintaining valve 43 is closed by the control unit 13. The balloon pump 61 and the second space 113 of the isolator 11 are thus cut off each other. Under this condition, the motor 123 drives the impeller turbine 122 in a counterclockwise direction (i.e. a positive direction shown by an arrow A in FIG. 2), and the silicon oil in the second space 113 is sucked by the fluid pump 12 through the path 21 and the first port 121a, and the pressure level in the second space will be reduced. The pressure level in the balloon pump 61 remains high because the pressure maintaining valve 43 is closed. When the pressure level in the second space 113 reaches a sufficiently low pressure level, the pressure maintaining valve 43 is opened by the control unit 13. In response to this operation, the pressure in the balloon pump 61 is introduced into the second space 113 in a burst and then the pressure level in the balloon pump 61 rapidly changes from high pressure to low pressure.

According to this rapid pressure operation, the balloon pump has high responsiveness.

In this present invention, the fluid pump 12 generates sufficient pressure fluctuations to generate pulsative operation of the pump used for supporting or substitution of cardiac function such as the blood pump or the balloon pump, and need not use an accumulation chamber to adjust the pressure. Therefore, the size of the pump driving unit can be minimized. Further, the fluid pump is smaller than a compressor, so that the pump driving unit can be miniaturized.

Further, in the present invention, the driving unit for driving the pump used for supporting or substitution of cardiac function has the isolator 11 that has divided first and second spaces 112 and 113, the fluid pump 12 that supplies silicon oil to the first space or sucks silicon oil from the first space 112, and the control unit 13 that operates the fluid pump 12. In response to supply and sucking operations of the fluid pump 12, pulsative operations are generated in the pump. Therefore, it is not necessary to use an accumulation chamber, and the driving unit size can be reduced.

Furthermore in the present invention, since the pump driving unit has a fluid pump that can be driven in either a positive or negative direction, no control valve is required to control fluid supply and sucking from the pump driving unit. Therefore, the pump driving unit can be manufactured at a lower cost.

According to the first embodiment, the pump driving unit uses the blood pump 51 as the pump used for supporting or substitution of a cardiac function. According to the second embodiment, the pump driving unit uses the balloon pump 61 as the pump used for supporting or substitution of a cardiac function. The present invention therefore enables a smaller pump driving unit.

What we claim is:

1. A pump driving unit for driving a pump used for supporting or substitution of cardiac function, comprising:
   a fluid pump for pulsatively driving said cardiac pump;
   an isolator configured to be connected to said fluid pump by a liquid space and to said cardiac pump by a gas space; and
   control unit configured to control said fluid pump,
   wherein said isolator is configured to form a first space and a second space divided from each other by a flexible member,
   said first space is configured to be connected to said fluid pump and said first space and said liquid space are filled with a liquid as an incompressible fluid, said second space is configured to be connected to said cardiac pump wherein said second space and said gas space are filled with a gas as a compressible fluid, and wherein said isolator transmits pressure change from said fluid space to said gas space, thereby acting as a pressure converter member to apply a driving force to said cardiac pump used for supporting or substitution of cardiac function.

2. The pump driving unit according to claim 1, wherein the second space is configured to be connected to the fluid pump as a blood pump.

3. The pump driving unit according to claim 1, wherein the second space is configured to be connected to the fluid pump as a balloon pump.

4. The pump driving unit according to claim 1, wherein the gas space is filled with air.

5. The pump driving unit according to claim 1, wherein the gas space is filled with helium gas.

6. The pump driving unit according to claim 1, further comprising a pressure maintaining valve disposed between the second space and the cardiac pump.

7. The pump driving unit according to claim 5, further comprising means for helium gas supply connected between the second space and the cardiac pump via an intake and exhaust valve.

8. The pump driving unit according to claim 1, wherein the fluid pump comprises an impeller turbine which is able to rotate in two directions, and a fluid is supplied to the first space when the impeller turbine is driven in a negative direction.

9. The pump driving unit according to claim 1, wherein the fluid pump comprises an impeller turbine which is able to rotate in two directions, and a fluid in the first space is sucked into the fluid pump when the impeller turbine is driven in a positive direction.

10. The pump driving unit according to claim 1, further comprising a first pressure sensor arranged at the first space, and a second pressure sensor arranged at the second space.

11. The pump driving unit according to claim 1, which comprises an intake and exhaust control valve mounted in communication with said gas space wherein said control unit is configured to control operation of said intake and exhaust control valve.

* * * * *